United States Patent
Kong et al.

(10) Patent No.: US 11,047,706 B2
(45) Date of Patent: Jun. 29, 2021

(54) PEDOMETER WITH ACCELEROMETER AND FOOT MOTION DISTINGUISHING METHOD

(71) Applicant: One Two Free Inc., Alhambra, CA (US)

(72) Inventors: Deming Kong, Shenzhen (CN); Guanxing Chen, Shenzhen (CN)

(*) Notice: Subject to any disclaimer, the term of this patent is extended or adjusted under 35 U.S.C. 154(b) by 206 days.

(21) Appl. No.: 15/339,848

(22) Filed: Oct. 31, 2016

(65) Prior Publication Data

US 2017/0241797 A1    Aug. 24, 2017

Related U.S. Application Data

(60) Provisional application No. 62/388,513, filed on Feb. 1, 2016.

(30) Foreign Application Priority Data

Feb. 5, 2016    (CN) .......................... 201610082327.7

(51) Int. Cl.
    *G01C 22/00*    (2006.01)
    *A43B 3/00*    (2006.01)
    (Continued)

(52) U.S. Cl.
    CPC .......... *G01C 22/006* (2013.01); *A43B 3/0005* (2013.01); *A61B 5/1123* (2013.01);
    (Continued)

(58) Field of Classification Search
    None
    See application file for complete search history.

(56) References Cited

U.S. PATENT DOCUMENTS 4,510,704 A * 4/1985 Johnson ................... A43B 3/00
                                                            36/136
4,649,552 A * 3/1987 Yukawa ............... G01C 22/006
                                                            235/105

(Continued)

FOREIGN PATENT DOCUMENTS

| EP | 2458338 A1 * | 5/2012 | ........... A61B 5/1036 |
| NL | 2324724 A1 * | 5/2011 | ............... A43B 3/00 |
| WO | WO-2014091583 A1 * | 6/2014 | ............... G01P 15/18 |

OTHER PUBLICATIONS

Hegde, Nagaraj; Bries, Matthew; and Sazonov, Edward—"A Comparative Review of Footwear-Based Wearable Systems"; Electronics 2016, 5, 48; doi:10.3390/electronics5030048; www.mdpi.com/journal/electronics (Year: 2016).*

*Primary Examiner* — Catherine T. Rastovski
*Assistant Examiner* — Leonard S Liang
(74) *Attorney, Agent, or Firm* — Raymond Y. Chan; David and Raymond Patent Firm

(57) ABSTRACT

A method for distinguishing a foot motion of a user by placing a pedometer at a foot of a user includes the steps of collecting an accelerating data from an accelerometer in a real time manner; filtering the accelerating data via a smoothing filter and a Kalman filter; generating a step data that represents number of steps taken by the user in response to the accelerating data through the smoothing filter; generating an activity data that represents a foot motion of the user in response to the accelerating data through the Kalman filter; and combining the step data and the activity data to form a resulted data that distinguishes the foot motion with step count of the user.

10 Claims, 13 Drawing Sheets

(51) Int. Cl.
*A61B 5/00* (2006.01)
*A61B 5/11* (2006.01)
*A63B 24/00* (2006.01)
*G16H 20/30* (2018.01)

(52) U.S. Cl.
CPC ............ *A61B 5/6807* (2013.01); *A61B 5/725* (2013.01); *A61B 5/112* (2013.01); *A61B 5/1116* (2013.01); *A61B 5/1118* (2013.01); *A61B 2560/029* (2013.01); *A61B 2562/0219* (2013.01); *A61B 2562/0247* (2013.01); *A63B 24/0062* (2013.01); *A63B 2220/40* (2013.01); *G16H 20/30* (2018.01)

(56) References Cited

U.S. PATENT DOCUMENTS

| | | | | | |
|---|---|---|---|---|---|
| 4,651,446 | A | * | 3/1987 | Yukawa | A43B 3/00 235/105 |
| 6,018,705 | A | * | 1/2000 | Gaudet | A61B 5/1121 235/105 |
| 6,493,652 | B1 | * | 12/2002 | Ohlenbusch | A61B 5/1038 324/160 |
| 6,611,789 | B1 | * | 8/2003 | Darley | A61B 5/1038 702/141 |
| 6,813,582 | B2 | * | 11/2004 | Levi | G01C 21/12 701/495 |
| 6,876,947 | B1 | * | 4/2005 | Darley | A43B 3/0005 702/160 |
| 6,882,955 | B1 | * | 4/2005 | Ohlenbusch | A43B 3/0005 702/160 |
| 7,225,565 | B2 | * | 6/2007 | DiBenedetto | A43B 1/0009 36/132 |
| 8,467,979 | B2 | * | 6/2013 | Sobolewski | A43B 1/0054 36/25 R |
| 8,676,541 | B2 | * | 3/2014 | Schrock | A43B 3/00 702/188 |
| 8,739,639 | B2 | * | 6/2014 | Owings | A43B 3/0005 73/862.046 |
| 2002/0040601 | A1 | * | 4/2002 | Fyfe | A63B 69/0028 73/490 |
| 2002/0143491 | A1 | * | 10/2002 | Scherzinger | G01C 21/16 702/160 |
| 2003/0009308 | A1 | * | 1/2003 | Kirtley | A61B 5/1038 702/141 |
| 2005/0033515 | A1 | * | 2/2005 | Bozzone | G01C 21/12 701/472 |
| 2007/0011919 | A1 | * | 1/2007 | Case, Jr. | A43B 1/0036 36/132 |
| 2008/0130691 | A1 | * | 6/2008 | Chen | H04N 5/4401 370/536 |
| 2008/0249740 | A1 | * | 10/2008 | Verhaert | G01C 21/16 702/160 |
| 2009/0221403 | A1 | * | 9/2009 | Chan | A63B 24/0062 482/8 |
| 2009/0235739 | A1 | * | 9/2009 | Morris Bamberg | A43B 7/00 73/379.05 |
| 2010/0184563 | A1 | * | 7/2010 | Molyneux | A43B 1/0054 482/1 |
| 2010/0292050 | A1 | * | 11/2010 | DiBenedetto | A63B 24/0062 482/9 |
| 2011/0054359 | A1 | * | 3/2011 | Sazonov | A43B 3/0005 600/595 |
| 2011/0119027 | A1 | * | 5/2011 | Zhu | G01C 22/006 702/160 |
| 2011/0304497 | A1 | * | 12/2011 | Molyneux | A43B 1/0054 342/42 |
| 2012/0041767 | A1 | * | 2/2012 | Hoffman | A63B 24/0059 705/1.1 |
| 2012/0083705 | A1 | * | 4/2012 | Yuen | A61B 5/0002 600/508 |
| 2012/0136573 | A1 | * | 5/2012 | Janardhanan | G01C 21/165 701/512 |
| 2013/0090881 | A1 | * | 4/2013 | Janardhanan | G06F 1/163 702/104 |
| 2013/0130843 | A1 | * | 5/2013 | Burroughs | A63B 71/0686 473/415 |
| 2013/0141233 | A1 | * | 6/2013 | Jacobs | G08B 19/00 340/521 |
| 2013/0197857 | A1 | * | 8/2013 | Lu | A61B 5/1122 702/141 |
| 2013/0247424 | A1 | * | 9/2013 | Tseng | A43B 3/0005 36/136 |
| 2013/0324890 | A1 | * | 12/2013 | Youssef | A61B 5/11 600/595 |
| 2014/0122012 | A1 | * | 5/2014 | Barfield | G01C 5/06 702/138 |
| 2014/0198227 | A1 | * | 7/2014 | Mohammad Mirzaei | G01C 21/12 348/208.2 |
| 2014/0273858 | A1 | * | 9/2014 | Panther | A61B 5/0002 455/41.2 |
| 2014/0275854 | A1 | * | 9/2014 | Venkatraman | A61B 5/721 600/301 |
| 2014/0278229 | A1 | * | 9/2014 | Hong | A63B 71/06 702/160 |
| 2014/0288435 | A1 | * | 9/2014 | Richards | A61B 5/02427 600/479 |
| 2014/0316305 | A1 | * | 10/2014 | Venkatraman | A61B 5/1112 600/595 |
| 2015/0243031 | A1 | * | 8/2015 | Narasimha | G06K 9/00268 382/103 |
| 2015/0258373 | A1 | * | 9/2015 | Molyneux | A43B 1/0054 700/91 |
| 2015/0285659 | A1 | * | 10/2015 | Curtis | G01C 22/006 702/97 |
| 2016/0007158 | A1 | * | 1/2016 | Venkatraman | H04W 4/023 455/456.2 |
| 2016/0113550 | A1 | * | 4/2016 | Martin | A61B 5/6898 600/595 |
| 2016/0231109 | A1 | * | 8/2016 | Chang | G01P 13/00 |
| 2016/0287937 | A1 | * | 10/2016 | Fitzgerald | G06K 9/00342 |
| 2016/0296144 | A1 | * | 10/2016 | Gaddam | G01C 21/20 |
| 2016/0325143 | A1 | * | 11/2016 | Yuen | G01P 7/00 |
| 2016/0334433 | A1 | * | 11/2016 | Kazemi | G01C 22/006 |
| 2016/0345865 | A1 | * | 12/2016 | Agrawal | A61B 5/1036 |
| 2017/0232294 | A1 | * | 8/2017 | Kruger | G09B 5/02 434/247 |
| 2019/0269353 | A1 | * | 9/2019 | Venkatraman | A61B 5/725 |
| 2020/0107607 | A1 | * | 4/2020 | Allen | G01R 33/0082 |

* cited by examiner

PEDOMETER WITH ACCELEROMETER AND FOOT MOTION DISTINGUISHING METHOD

CROSS REFERENCE OF RELATED APPLICATION

This is a non-provisional application that claims the benefit of priority under 35 U.S.C. § 120 to a provisional application, application No. 62/388,513, filed May 19, 2016, and claims the benefit of priority under 35 U.S.C. 119(a-d) to Chinese application number 201610082327.7, filed Feb. 5, 2016. The afore-mentioned patent applications are hereby incorporated by reference in their entireties.

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to apparatus for step counting, and more particularly to a pedometer with an accelerometer and foot motion distinguishing method, which not only accurately records number of steps taken by a user but also precisely distinguish the foot motion of the user to differentiate the user movement of walking, jogging and running.

Description of Related Arts

Motion capturing technique is a conventional process of recording user movement via an image capturing device. Through the video or sequential images being captured, the user is able to determine number of steps taken by the user within a traveled distance and to differentiate the user movement of walking, jogging and running. However, such method has several drawbacks. The image capturing device must be operated under bright environment in order to capture clear and good quality of images. In addition, the operation of the image capturing device is limited by the setup location of the image capturing device, the place where the user exercise, and the traveled distance. In other words, the image capturing device must be set up at a location that the foot motion of the user can be captured, such as in front of the user. The image capturing device must be located in an open area to capture the foot motion of the user. In addition, the video clip captured in the image capturing device will be digitally saved in a memory thereof. Therefore, when the traveled distance is relatively long, the size of the video clip will be extremely large that the image capturing device will not be able to save the video clip in the limited memory space. A sensor apparatus is recently introduced to detect the motion of the user. The sensor apparatus is relatively inexpensive, is relative small to carry, and is not limited by the environment. For example, the sensor apparatus can be incorporated with a monitoring device for monitoring the disabilities or the detectors for prevention of sudden illness or emergency. Generally speaking, the sensor apparatus comprises an accelerometer, a gyroscope, and a microphone. It is commonly found that the sensor apparatus is built-in with the existing electronic device, such as mobile phone "Apple Iphone" and game controller "Nintendo Wiimote". The electronic device has a wireless capability to wirelessly transmit the data from the sensor apparatus. Therefore, the sensor apparatus is widely used in different fields such as in an intelligent home control system.

However, there are several drawbacks for the sensor apparatus. Firstly, the output data from the sensor apparatus cannot be rapidly divided. In particular, it is extremely complicated to segment the accelerating data of the accelerometer from the output data of the sensor in a real time manner. In other words, the output data from the sensor must be completely transmitted to a central processor to process the output data and segment the accelerating data from the output data. It is time consuming and requires relatively large computing power. Secondary, the output data from the sensor apparatus cannot be modularized and formed different classification models. In other words, the output data cannot be automatically analyzed to effectively distinguish different exercises performed by the user. Thirdly, there is no effective method to enhance the interaction of the user to notify the user the result right after the workout is completed.

Regarding the date segmentation, many powerful electronic devices incorporate with an advanced algorithm to manually segment the accelerating data from the output data of the sensor apparatus in order to build a database for training and testing purpose. This algorithm can minimize the workload of the central processor for data processing and idealize the data. In other words, errors or deviations will be omitted in the collected accelerating data for analysis. However, the algorithm will minimize the interaction and will not be practically executed in different applications. Therefore, it would be better to segment the accelerating data from the output data in a real time manner. There are two common algorithms for date segmentation, which are Dynamic Time Warping (DTW) and Hidden Markov Model (HMM) as non-linear sequence alignment algorithm.

Dynamic Time Warping (DTW) is an algorithm for measuring similarity between two temporal sequences which may vary in time or speed. The advantage of using DTW is that it requires relatively less amount of data to be processed and is able to dynamically update and match with the template. However, the disadvantage of using DTW is that it is much too slow and memory consuming for aligning large sequences due to the time and memory complexity. Hidden Markov Model (HMM) is also an algorithm for dynamically representing a state or condition at one moment for activity recognition. However, the human body movements are much complicated that the activity of the user cannot be accurately recognized by a single HMM module.

SUMMARY OF THE PRESENT INVENTION

The invention is advantageous in that it provides a pedometer with an accelerometer and foot motion distinguishing method, which not only accurately records number of steps taken by a user but also precisely distinguish the foot motion of the user to differentiate the user movement of walking, jogging and running.

Another advantage of the invention is to provide a pedometer with an accelerometer and foot motion distinguishing method, wherein the step count can be simply obtained by filtering accelerating data through the smoothing filter so as to accurately determine number of steps taken by the user.

Another advantage of the invention is to provide a pedometer with an accelerometer and foot motion distinguishing method, wherein the activity of the user, such as walking, jogging, or running, can be simply distinguished by filtering accelerating data through the Kalman filter.

Another advantage of the invention is to provide a pedometer with an accelerometer and foot motion distinguishing method, wherein the motion posture of the user can be easily distinguished by comparing the wave form from the resultant acceleration, so as to determine the motion posture of the user. In particular, the running posture of the user can be distinguished such as pressuring on the front soles portion of the user, pressuring on a full soles portion of the user, or pressuring on the heel portion of the user. In addition, the present invention is able to distinguish the up-the-stairs posture, down-the-stairs posture of the user, and jogging posture of the user.

Another advantage of the invention is to provide a pedometer with an accelerometer and foot motion distinguishing method, which can be placed at any foot location, such as embedding the pedometer the shoe sole or holding the pedometer on the shoe vamp.

Another advantage of the invention is to provide a pedometer with an accelerometer and foot motion distinguishing method, which does not require to alter the original structural design of the shoe, so as to minimize the manufacturing cost of the shoe incorporating with the pedometer.

Another advantage of the invention is to provide a pedometer with an accelerometer and foot motion distinguishing method, wherein no expensive or complicated structure is required to employ in the present invention in order to achieve the above mentioned objects. Therefore, the present invention successfully provides an economic and efficient solution for accurately counting number of steps taken by the user and for precisely distinguishing the foot motion of the user to differentiate the user movement of walking, jogging and running.

Additional advantages and features of the invention will become apparent from the description which follows, and may be realized by means of the instrumentalities and combinations particular point out in the appended claims.

According to the present invention, the foregoing and other objects and advantages are attained by a method for distinguishing a foot motion of a user by placing a pedometer at a foot of a user, which comprises the following steps executed by a computerize device.

(1) Collect an accelerating data from an accelerometer of the pedometer in a real time manner. Accordingly, the accelerating data is extracted from X axis, Y axis, and Z axis to obtain X value, Y value, and Z value of the accelerating data respectively, wherein the X axis refers to a foot motion in a forward direction, the Y axis refers to a foot motion in a left-and-right direction, and the Z axis refers to a foot motion in an elevated direction.

(2) Filter the accelerating data via a smoothing filter and a Kalman filter. The accelerating data from the accelerometer is duplicated to form two sets of identical accelerating data that a first set of accelerating data is processed via the smoothing filter and a second set of accelerating data is processed via the Kalman filter.

(3) Generate a step data that represents number of steps taken by the user in response to the accelerating data through the smoothing filter.

(4) Generate an activity data that represents a foot motion of the user in response to the accelerating data through the Kalman filter.

(5) Combine the step data and the activity data to form a resulted data that distinguishes the foot motion with step count of the user.

In accordance with another aspect of the invention, the present invention comprises a pedometer, comprising:

a casing adapted for being placing at a foot of a user;

an accelerometer, which is received in the casing, that collects an accelerating data in a real time manner;

a smoothing filter filtering the accelerating data to generate a step data that represents number of steps taken by the user;

a Kalman filter filtering the accelerating data to generate an activity data that represents a foot motion of the user; and a processor combining the step data and the activity data to form a resulted data that distinguishes the foot motion with step count of the user.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

A pedometer 10 with an accelerometer 20 and foot motion distinguishing arrangement, which not only accurately records number of steps taken by a user but also precisely distinguish the foot motion of the user to differentiate the user movement of walking, jogging and running.

Figure 10:
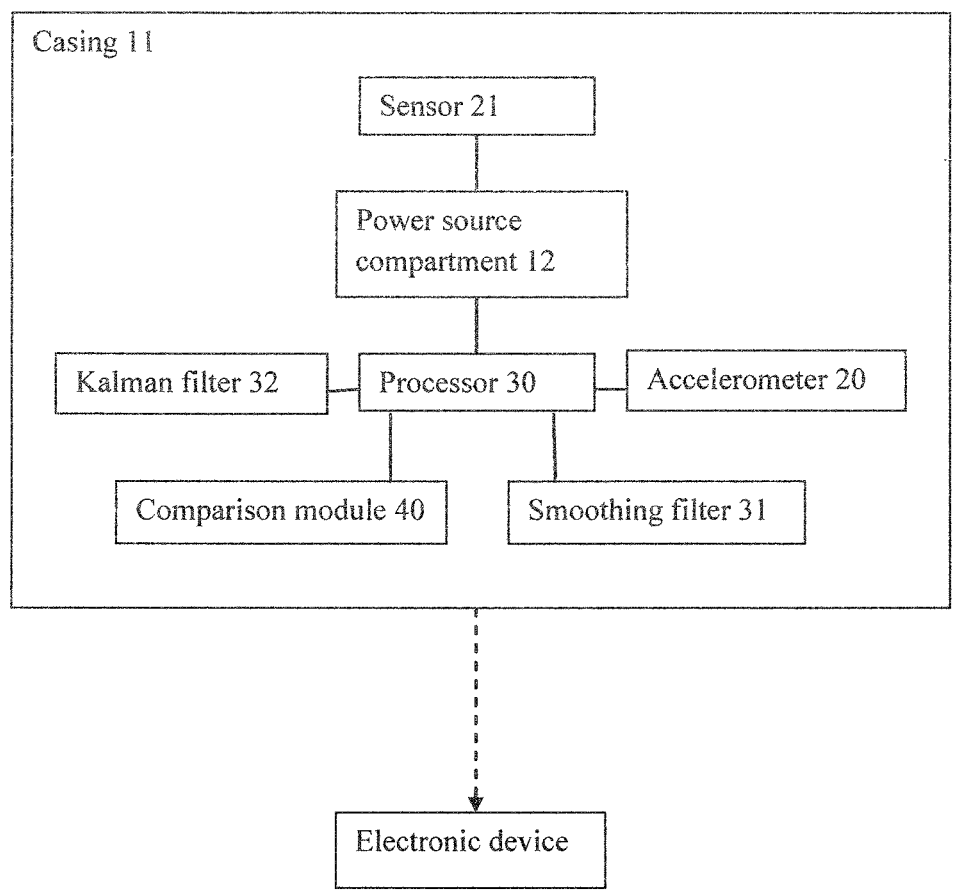
FIG. 10 is a block diagram of the pedometer according to the above preferred embodiment of the present invention.

As shown in FIG. 10, the pedometer 10 comprises a casing 11 adapted for being placing at a foot of a user, a processor 30 such as a microcontroller unit (MCU), and a comparison module 40. The casing 11 has a power source compartment 12 for receiving a power source, such as a replaceable watch battery or rechargeable watch battery, wherein the accelerometer 20 is received in the casing 30 to electrically linked to the power source in the power source compartment 12.

The accelerometer 20 is initiated to define a X axis, a Y axis, and a Z axis. The X axis refers to a foot motion in a forward direction. The Y axis refers to a foot motion in a left-and-right direction, wherein when the foot moves to the left direction, the value of Y axis is positive and when the foot moves to the right direction, the value of Y axis is negative. The Z axis refers to a foot motion in an elevated direction, wherein when the user elevates the foot, the value of Z axis is negative, and when the user lowers the foot, the value of Z axis is positive. It is worth mentioning that the accelerometer 20 is initiated to automatically define the X axis, Y axis, and Z axis to obtain X value, Y value, and Z value of the accelerating data. For example, when the pedometer 10 is horizontally supported, such as embedded in the shoe sole in FIG. 11, the accelerometer 20 is initiated to automatically define the X axis, Y axis, and Z axis with respect to the horizontal pedometer 10. When the pedometer 10 is inclinedly supported, such as being held on the shoe vamp as shown in FIG. 12, the accelerometer 20 can also be initiated to automatically define the X axis, Y axis, and Z axis with respect to the inclined pedometer 10.

According to the preferred embodiment, the pedometer 10 is automatically activated by a sensor 21. The sensor 21 can be a pressure sensor and/or a motion sensor. For example, when the pedometer 10 is embedded in the shoe sole, the pressure sensor can be used. Therefore, when the user applies pressures, such as walking or running, the pedometer 10 will be automatically activated to activate the accelerometer 20 for data collection. Likewise, when the pedometer 10 is held on the shoe vamp, the motion sensor can be used. Therefore, when the user moves his or her foot, such as walking or running, the pedometer 10 will also be automatically activated to activate the accelerometer 20 for data collection.

The method comprises the following steps, which are executed by a computerized device.

(1) Collect the accelerating data from the accelerometer 20 placed at one foot of the user in a real time manner. For example, the pedometer 10 can be embedded in the shoe sole, preferably at the mid portion thereof between the toe and heel portions. Alternatively, the pedometer 10 can be held on the shoe vamp via the shoe tie. It is worth mentioning that the pedometer 10 is only held at one foot of the user.

(2) Process and filter the collected accelerating data via a smoothing filter 31 and a Kalman filter 32 to smooth the collected accelerating data and to minimize deviation thereof. Accordingly, the accelerating data from the accelerometer 20 is duplicated by the processor 30 to form two sets of identical accelerating data via the processor 30. The first set of accelerating data is processed via the smoothing filter 31 and the second set of accelerating data is processed via the Kalman filter 32.

(3) Generate a step data that represents number of steps taken by the user in response to the collected accelerating data through the smoothing filter 31. Accordingly, the processor 30 will generate the step data after the accelerating data is filtered by the smoothing filter 31.

(4) Generate an activity data that represents a foot motion of the user in response to the collected accelerating data through the Kalman filter 32. Accordingly, the processor 30 will generate the activity data after the accelerating data is filtered by the Kalman filter 32.

(5) Combine the step data and the activity data via the processor 30 to form a resulted data that distinguishes the foot motion with step count of the user.

According to the preferred embodiment, the present invention uses Fused HMM algorithm to obtain two or more temporal sequences at the same time, so as to ensure the enhance the interaction and characterization for dynamically representing a state or condition at one moment for activity recognition. If one of the HMM fails to obtain the data, another HMM is able to pick the data to ensure the stability of the system. The present invention will obtain the data in response to the activity of the user and project for estimating the following data so as to make more accurate predictions. In other words, before the workout of the user is completed, the resulted data is already processed that distinguishes the foot motion with step count of the user.

In the step (3), the accelerating data is processed through the smoothing filter 31 to obtain smooth step data by the moving average method in a scale space, wherein every two consequent accelerating data will be averaged to from the smooth accelerating data. The size of the scale space is directly related to the smoothing effect. The smoothing effect will be enhanced by increasing the scale space. However, if the scale space is extremely large, marginal information will be lost through the smoothing process, such that the output value of the smoothing filter 31 will be vague. In addition, the wave form through the smoothing filter 31 will lag that it cannot distinguish the motion posture of the user. On the other hand, the accelerating data is processed through the smoothing filter 31 can be accurately determine number of steps taken by the user.

The accelerating data is extracted along three axes, i.e. X axis, Y axis, and Z axis. The values of X axis, referring to X values, are continuously collected in a real manner to form a temporal sequence of X value. A X threshold (Ax) is preset to compare with the X value via the comparison module 40, wherein each of X values in sequence is collected and compared with the X threshold. It is counted as one step motion of the user when the previous X value is smaller than the X threshold and the following X value is larger than the X threshold. In other words, when the user lifts his or her foot, the X value is smaller than the X threshold. When the user drops his or her foot, X value is larger than the X threshold. Therefore, it is counted as one step motion of the user when the user drops his or her foot and then drops his or her foot. Due to the error or noise during the data collection, the X values are collected that the values thereof are fluctuated close to the X threshold in response to one step motion of the user. Once the X values are compared with the X threshold, more than one step will be counted. In order to reduce the error, the data collection is configured that the accelerometer 20 is set at 25 Hz. Since normal human will not able to take five steps in one second, no more than 5 steps will be counted within 25 consequent X values. It is worth mentioning since the pedometer 10 is only located at one foot of the user, such as provided at one shoe worn by the user, the foot motion is counted to have no more than 3 steps when the user walks 5 steps. In other words, the step count will not be exceed 3 steps in one second, such that 8 or more consequent X values will be collected for counting one step motion. As a result, the pedometer 10 of the present invention can accurately count the footsteps of the user by using this algorithm.

In the step (4), the accelerating data is processed through the Kalman filter 32 to obtain the activity data by optimizing prediction that produces estimates of the current state variables, so as to smooth the wave form of the activity data. Therefore, the wave form of the activity data can be analyzed for distinguishing the motion posture of the user.

The activity data is analyzed to define an activity periodicity, wherein different activities have different activity periodicities. In addition, different wave forms represent different activities in each activity periodicity. As a result, each wave form can be distinguished for a particular motion posture of the user.

The value of the activity data is directly related to the intensity of the activity of the user. In other words, different values of the activity data are directly related to activity of walking, jogging, and running in response to a value of a resultant acceleration. Accordingly, the resultant acceleration can be determined via the processor 30 by the following formulas.

$$a=\sqrt{(a\_x^2+a\_y^2+a\_z^2)}$$

a refers to the resultant acceleration, a_x, a_y, and a_z refer to accelerating data from X axis, Y axis, and Z axis respectively.

An average resultant acceleration a' is determined by averaging the values of a within a period. Therefore, the value of a' will represents the activity of walking or running. In other words, the activity of walking will have smaller value of a', and the activity of running will have bigger value of a'. After the activity of the user is distinguished, the characteristic value of the wave form is obtained by further data analysis. Therefore, the characteristic value of the wave form is classified to distinguish the motion posture of the user. Accordingly, the characteristic value of the wave form is obtained by an average value, a mean difference, a quartile deviation, a variation coefficient, and a skewness of the wave form in one period to distinguish the motion posture of the user.

Figure 1:
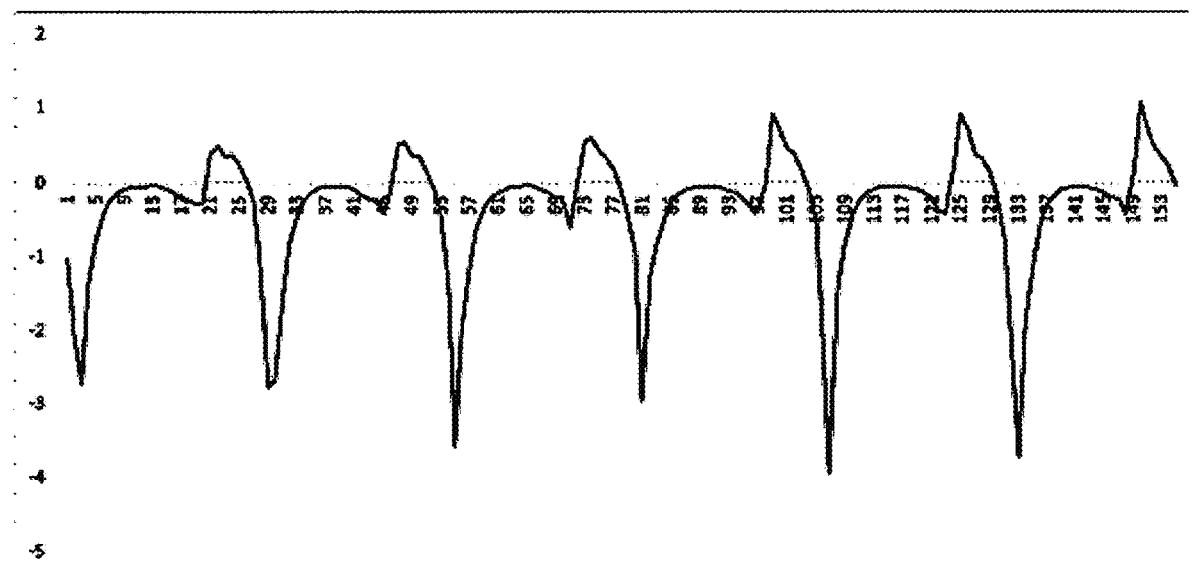
FIG. 1 is a graph illustrating an accelerating data along a X axis generated by a pedometer according to a preferred embodiment of the present invention.
Figure 2:
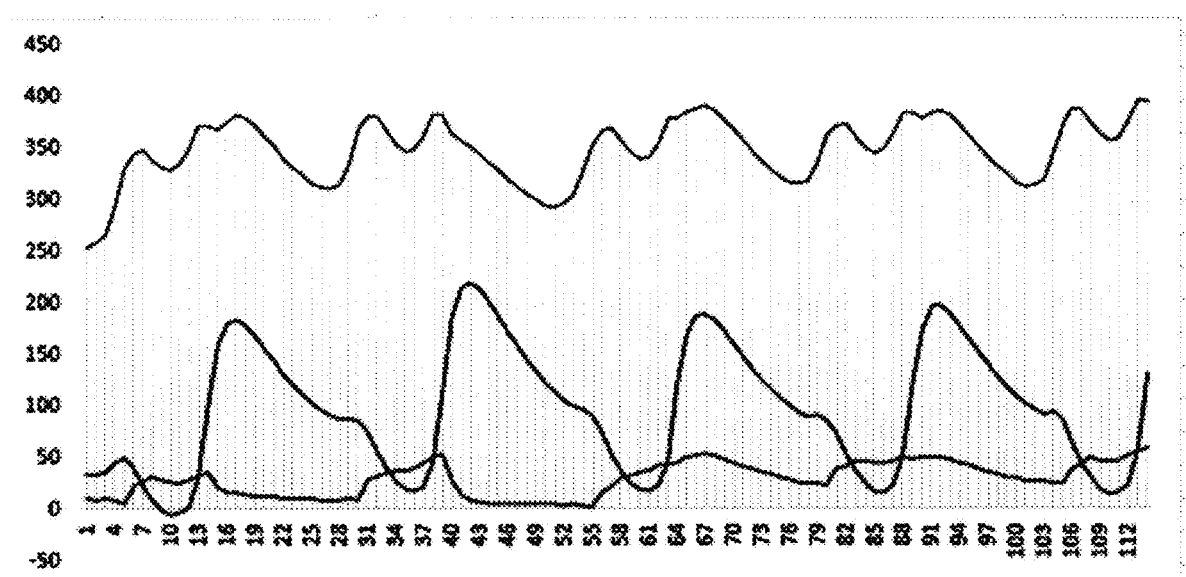
FIG. 2 is a graph illustrating an accelerating data processed through a Kalman filter according to the above preferred embodiment of the present invention.
Figure 3:
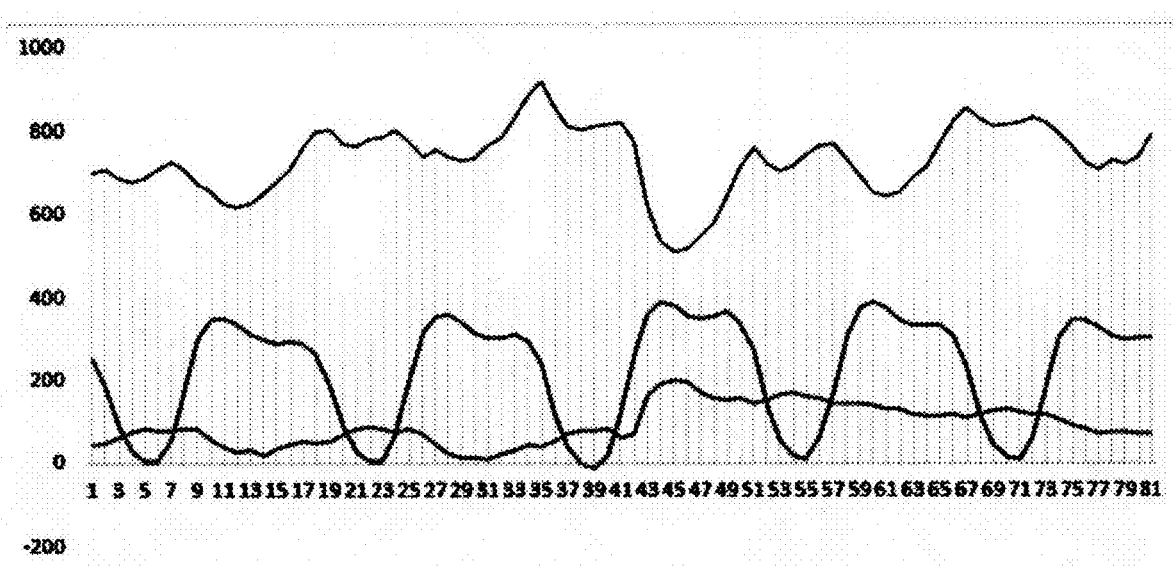
FIG. 3 is a graph illustrating the accelerating data processed through the Kalman filter according to the above preferred embodiment of the present invention, illustrating the wave form of the activity data representing running activity via a front soles portion of the user stepping on a ground surface.
Figure 4:
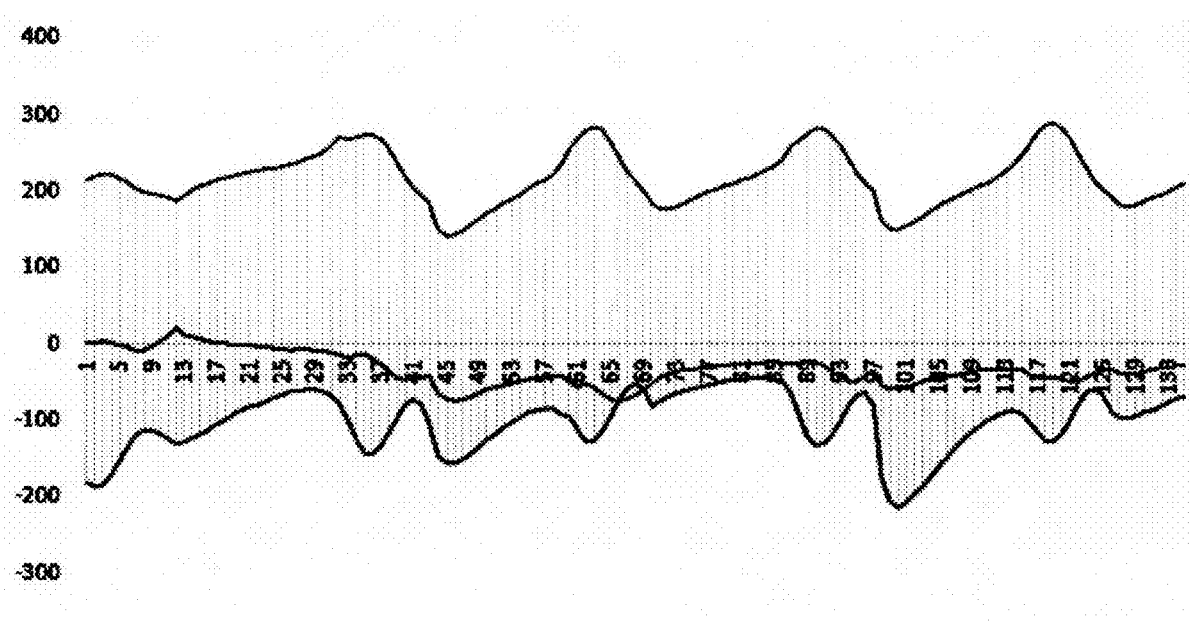
FIG. 4 is a graph illustrating the accelerating data processed through the Kalman filter according to the above preferred embodiment of the present invention, illustrating the wave form of the activity data representing on-the-stairs activity.
Figure 5:
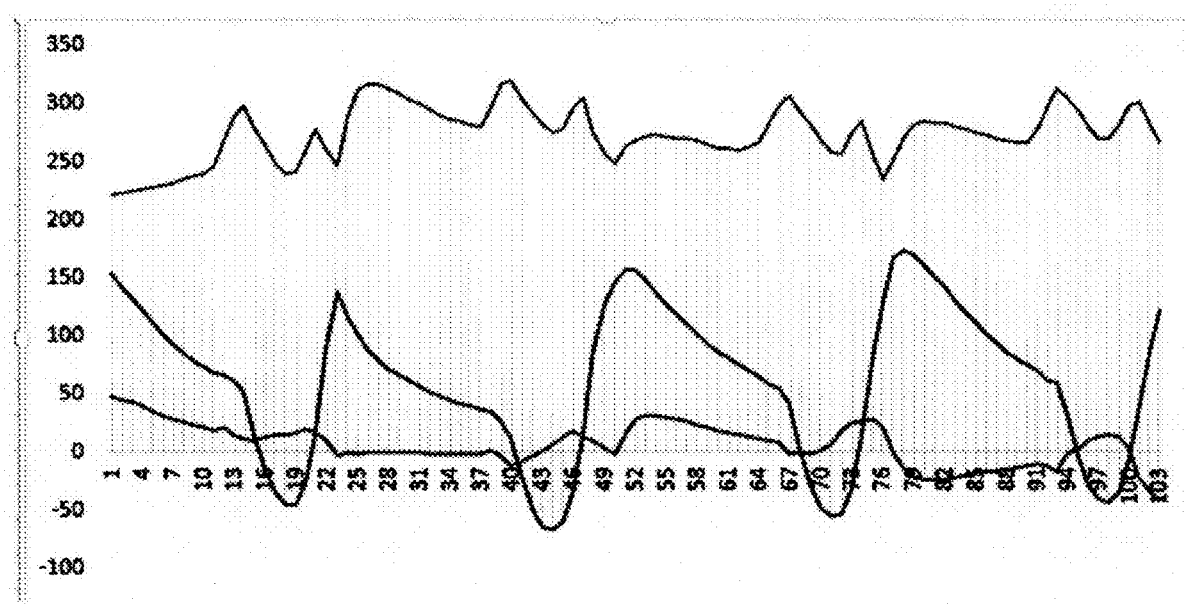
FIG. 5 is a graph illustrating the accelerating data processed through the Kalman filter according to the above preferred embodiment of the present invention, illustrating the wave form of the activity data representing down-the-stairs activity.
Figure 6:
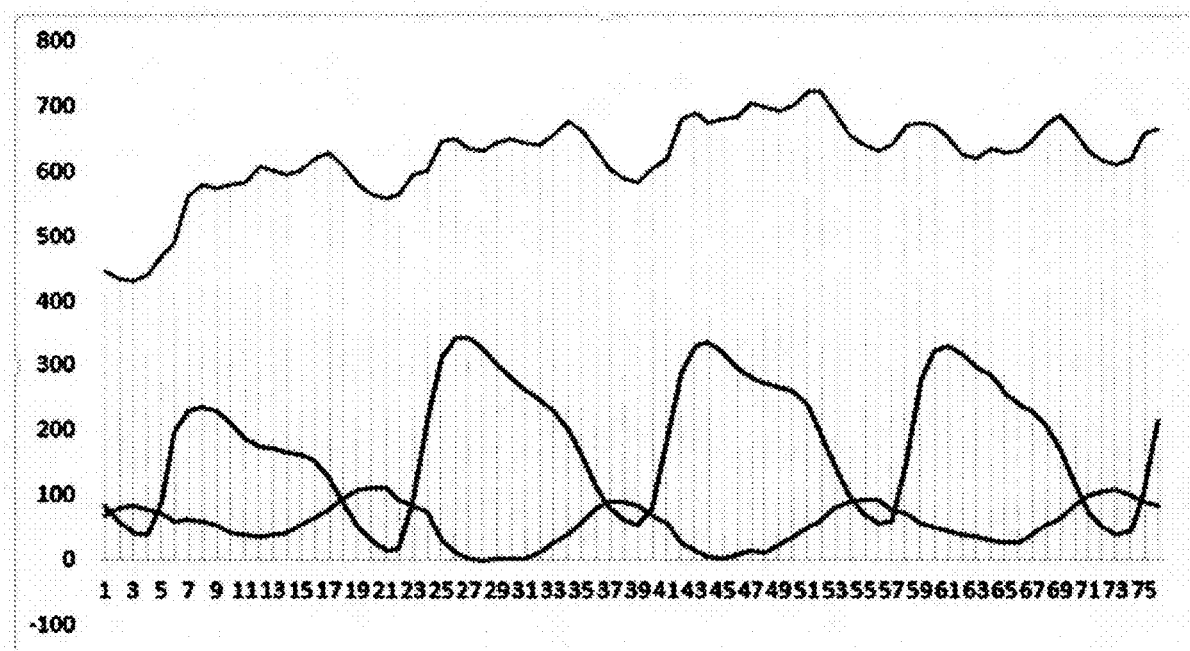
FIG. 6 is a graph illustrating the accelerating data processed through the Kalman filter according to the above preferred embodiment of the present invention, illustrating the wave form of the activity data representing running activity via a full soles portion of the user stepping on a ground surface.
Figure 7:
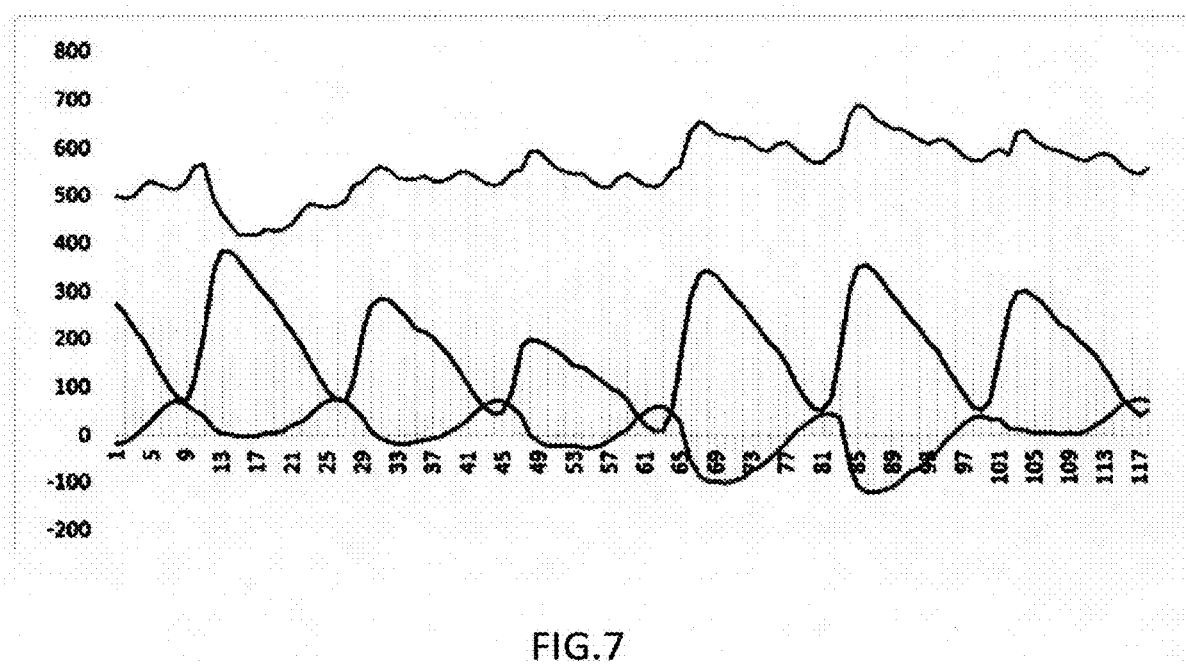
FIG. 7 is a graph illustrating the accelerating data processed through the Kalman filter according to the above preferred embodiment of the present invention, illustrating the wave form of the activity data representing running activity via a heel portion of the user stepping on a ground surface.
Figure 8:
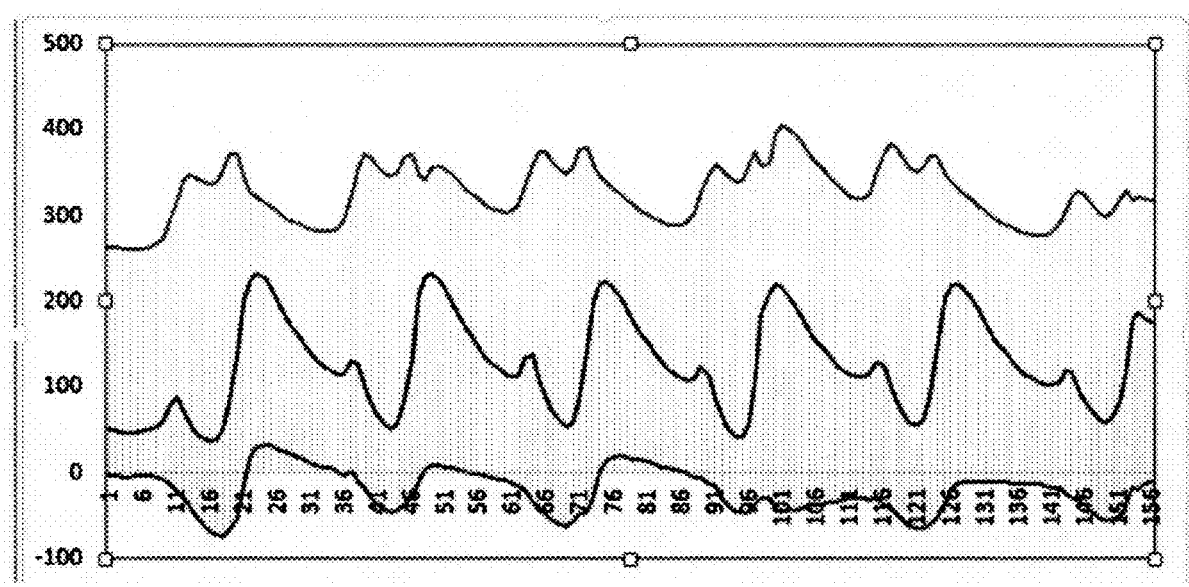
FIG. 8 is a graph illustrating the accelerating data processed through the Kalman filter according to the above preferred embodiment of the present invention, illustrating the wave form of the activity data representing jogging activity.
Figure 9:
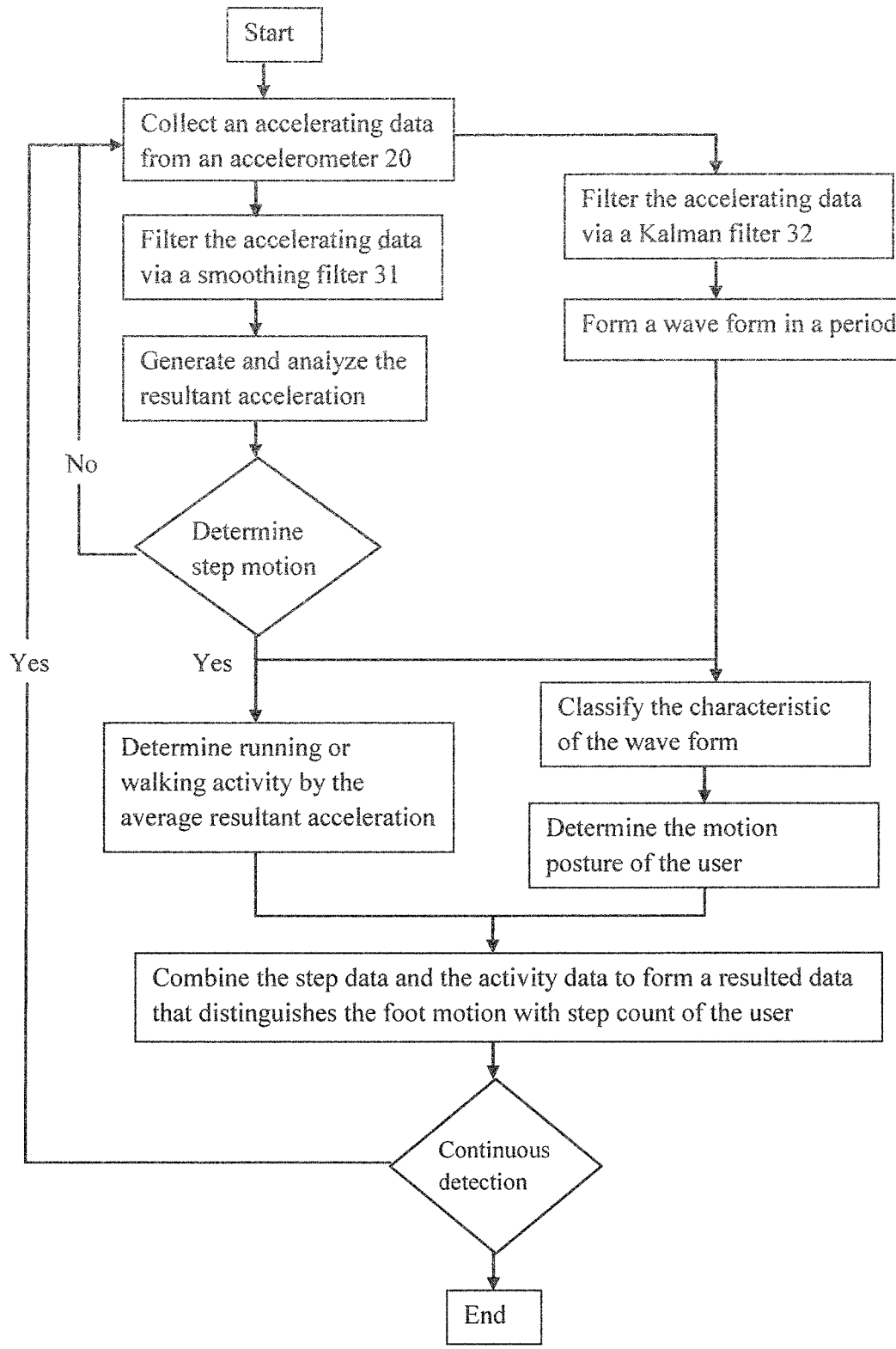
FIG. 9 is a flow chart of the foot motion distinguishing method according to the above preferred embodiment of the present invention.

In particular, a plurality of wave form configurations are pre-stored to compare the wave form in response to the resultant acceleration via the comparison module 40. FIG. 4 illustrates the wave form of the activity data representing running activity via a front soles portion of the user stepping on a ground surface. FIG. 6 illustrates the wave form of the activity data representing running activity via a full soles portion of the user stepping on the ground surface. FIG. 7 illustrates the wave form of the activity data representing running activity via a heel portion of the user stepping on the ground surface. Therefore, by comparing the wave form, the present invention is able to distinguish the running posture of the user. FIGS. 4 and 5 illustrate the wave form of the activity data representing on-the-stairs activity and down-the-stairs activity respectively. In other words, through the comparison of the wave form, the present invention is able to distinguish the up-the-stairs posture or down-the-stairs posture of the user. FIG. 8 illustrates the wave form of the activity data representing jogging activity, therefore, the present invention is able to distinguish the jogging posture of the user.

Figure 11:
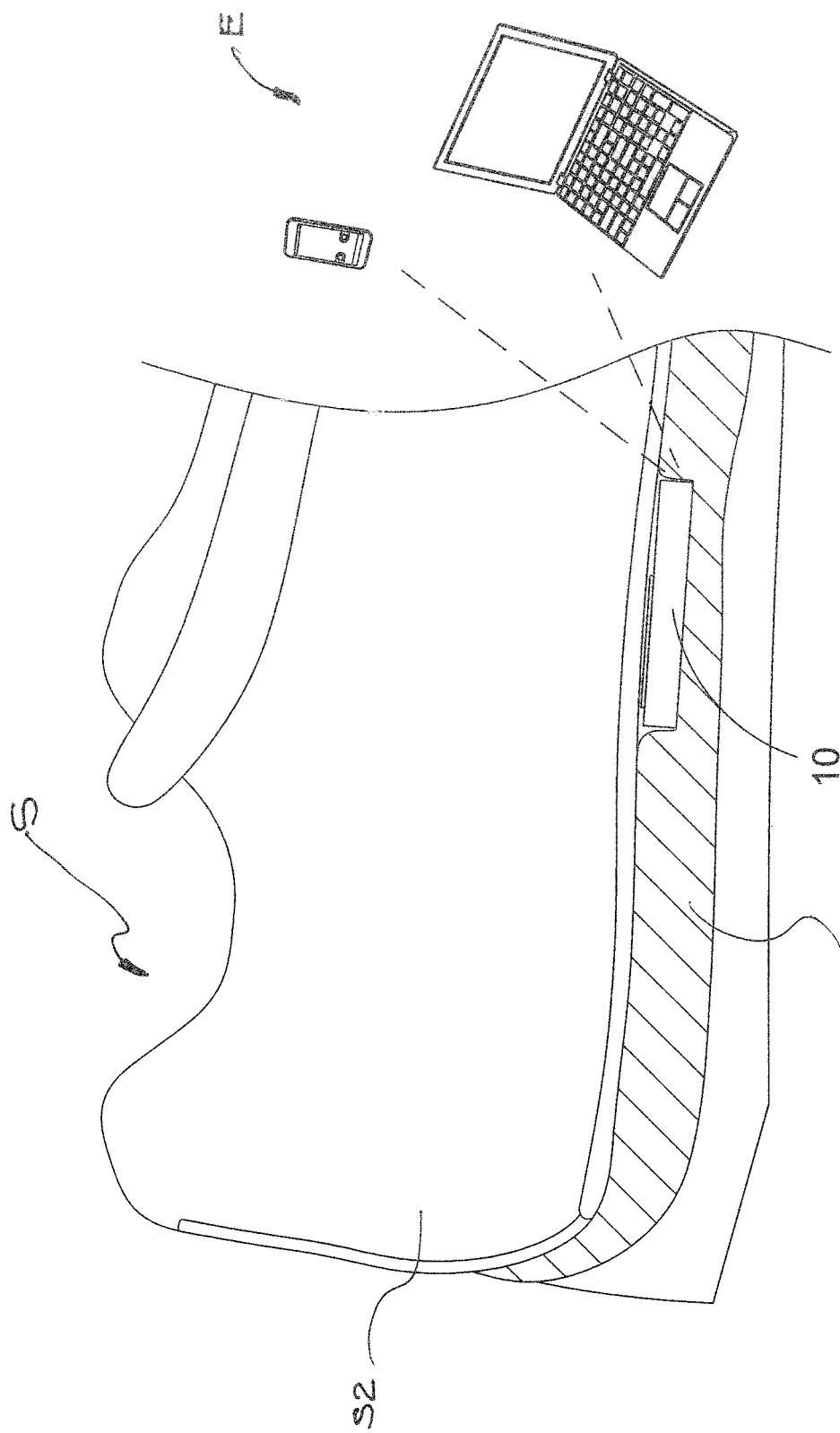
FIG. 11 illustrates the pedometer embedded in a shoe sole of a shoe according to the above preferred embodiment of the present invention.
Figure 12:
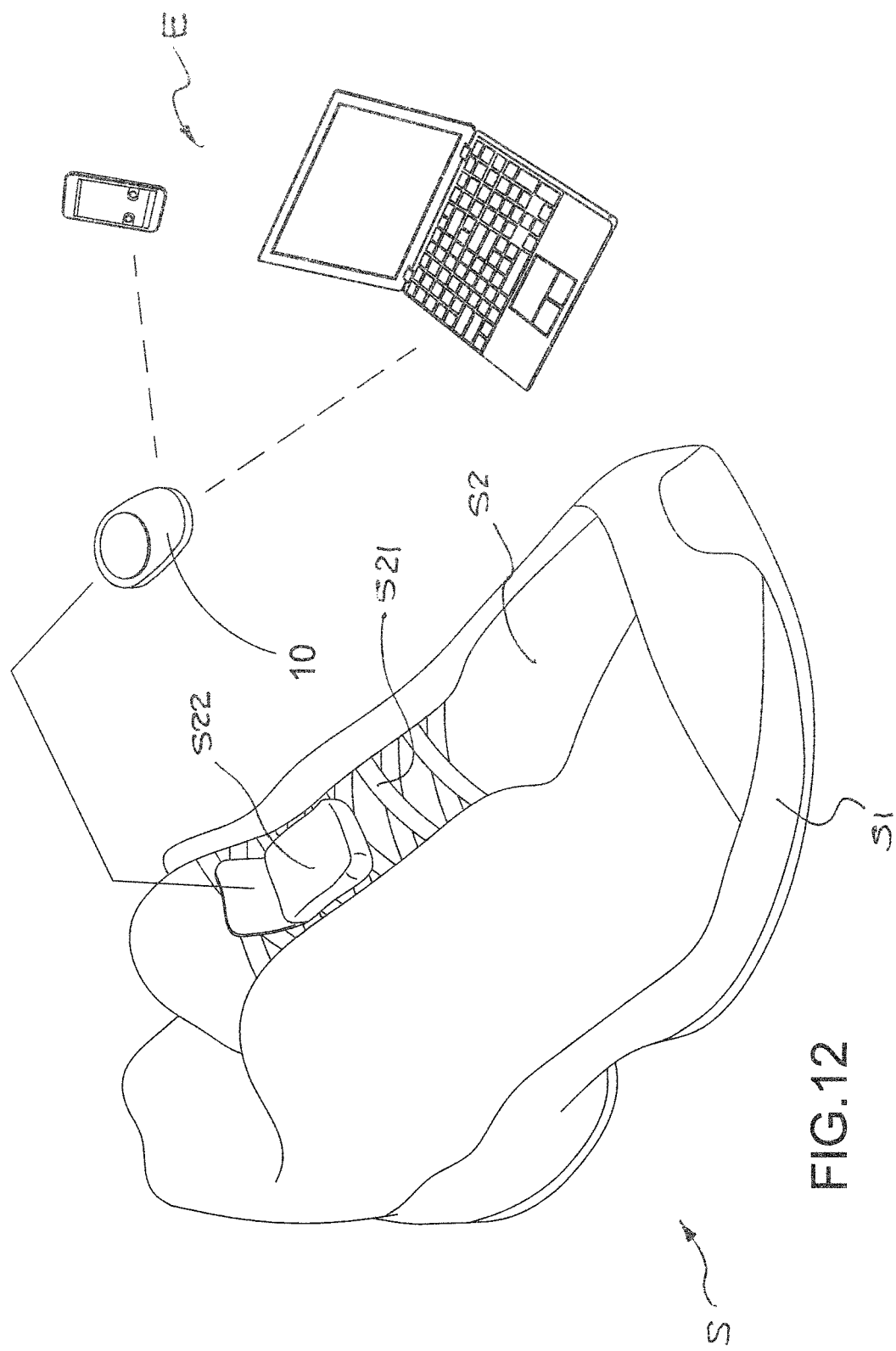
FIG. 12 illustrates the pedometer held on a shoe vamp of a shoe according to the above preferred embodiment of the present invention.

According to the preferred embodiment, the pedometer 10 of the present invention can be wirelessly linked to an electronic device E (as shown in FIGS. 11 and 12) such as mobile phone, a portable pedometer processing device, a tablet, or a computer via a wireless link, as shown in FIG. 10. The wireless link can be "WiFi", "Bluetooth", NFC, or other wireless connection. Therefore, the accelerating data can be processed in the pedometer 10, wherein the resulted data will then be wirelessly transmitted to the electronic device E.

Figure 10A:
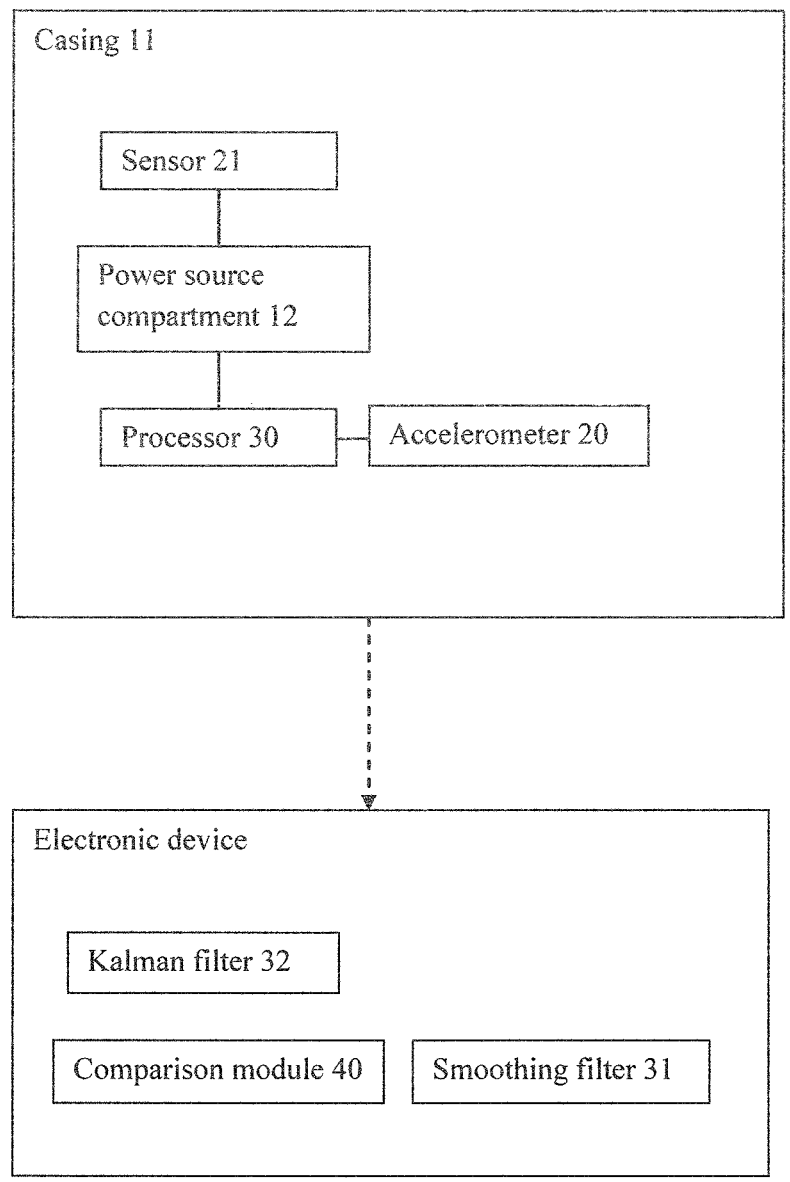
FIG. 10A is a block diagram of an alternative mode of the pedometer according to the above preferred embodiment of the present invention.

Alternatively, the accelerating data from the accelerometer 20 can be directly transmitted to the electronic device E, wherein the accelerating data can be processed in the electronic device. Accordingly, the smoothing filter 31, the Kalman filter 32, and the comparison module 40 are provided in the electronic device E, as shown in FIG. 10A. Therefore, the accelerating data can be processed in a processing unit of the electronic device E. In the embodiment and its alternative mode, the resulted data will be displayed by a screen of the electronic device.

Referring to FIGS. 11 and 12, the pedometer 10 is preferred to be carried by a shoe S to be worn by the user, wherein the pedometer 10 is preferred to be installed at a position of the shoe S where no substantial bending or deforming of the shoe while walking, jogging and running activities of the user. For example, as shown in FIG. 11, a receiving cavity S11 is provided at a middle portion of a shoe sole S1 of the shoe S for receiving the pedometer 10 therein. Alternatively, as shown in FIG. 12, a container S22 is attached to the shoe string S21 of the shoe body S2 coupled on top of the shoe sole S1 of the shoe S, and the pedometer 10 is received in the container S22.

It is appreciated that when the user is a child wearing the shoe S, the pedometer 10 of the present invention not only can determine the activity of the child that whether he or she is walking, jogging and running, but also can record the activity of the child user for health monitoring and exercise planning by the parents. If a positioning device is further included in the pedometer 10, the parents may even track the location of the child user for security purpose.

In addition, when the user, who wears the shoe S carrying the pedometer 10 of the present invention, is an old man or woman or a patient required attention by the physician or his or her family member, the pedometer 10 may also installed with a positioning device and a communication device, wherein activities of the aged user or patient user can be monitored and reported by the pedometer 10 to the physician or family member who have the electronic device E communicating with the pedometer 10. The activity of walking, jogging and running of the aged user or patient user can be recorded and determined whether it is normal or whether there may be any risk to the aged user or patient user going to happen for physical education and safety purposes.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A pedometer for recording number of steps taken by a user and distinguishing foot motions of the user to differentiate the user movement of walking, jogging and running, comprising:

a casing configured for being placed at a foot of the user;

a power source received in the casing;

an accelerometer received in the casing and electrically linked to the power source, wherein the accelerometer defines a X axis referring to a foot motion in a forward direction, a Y axis referring to a foot motion in a left-and-right direction, and a Z axis referring to a foot motion in an elevated direction, wherein accelerating data is extracted to obtain X values, Y values and Z values of accelerating data of the foot along the X axis, the Y axis and the Z axis respectively, wherein the accelerometer is configured for being positioned at a mid portion between a toe portion and a heel portion of the foot and collect accelerating data in a real time manner;

a smoothing filter and a Kalman filter arranged to process and filter the accelerating data collected from the accelerometer to smooth the acceleration data and to minimize deviation of the acceleration data;

a processor arranged to duplicate the accelerating data from the accelerometer to form a first set of accelerating data processed via the smoothing filter and a second set of accelerating data processed via the Kalman filter, such that the processor generates step data representing a number of steps taken by the user in response to the accelerating data collected from the accelerometer after the accelerating data is filtered by the smoothing filter, and generates activity data representing the foot motion of the user in response to the accelerating data from the accelerometer after the accelerating data is filtered by the Kalman filter, wherein the step data and the activity data are combined by the processor to form a resulted data that distinguishes the foot motion with step count of the user; and a comparison module arranged to preset a X threshold, wherein the X values of the X axis are continuously collected by the accelerometer in the real time manner to form a temporal sequence of X values, wherein each of the X values in sequence is collected and compared with the X threshold via the comparison module in such a manner that one of the step motions of the user is counted when a previous X value of the X values is smaller than the X threshold while the foot of the user is lifted and a following X value of the X values is larger than the X threshold when the foot of the user is dropped back, thereby footsteps of the user is able to be counted by the pedometer;

wherein the accelerating data from the accelerometer is processed through the Kalman filter to obtain activity data that produces estimates of current state variables so as to smooth a wave form of the activity data which is able to be analyzed by the processor to define an activity periodicity for distinguishing a motion posture of the user, wherein a value of the activity data is related to an intensity of an activity of the user such that different values of the activity data are related to activity of walking and running in response to a value of a resultant acceleration which is determined by $$a = \sqrt{(a\_x^2 + z\_y^2 + a\_z^2)},$$

wherein a refers to the resultant acceleration, a_x, a_y, and a_z refer to accelerating data from the X axis, the Y axis and the Z axis respectively, wherein an average resultant acceleration a' is determined by averaging the values of a within a period, so that a smaller value of the average resultant acceleration a' represents an activity of walking while a bigger value of the average resultant acceleration a' represents an activity of running.

2. The pedometer, as recited in claim 1, wherein a plurality of wave form configurations are pre-stored to compare the wave form in response to the resultant acceleration via the comparison module, wherein by comparing the wave form with the wave form configurations pre-stored, the pedometer is able to distinguish a running posture of the user, an on-the-stairs activity, a down-the stairs activity, and a jogging posture of the user.

3. The pedometer, as recited in claim 1, wherein the smoothing filter, the Kalman filter, the comparison module and the processor are provided in an electronic device which is wirelessly linked to the accelerometer received in the casing.

4. The pedometer, as recited in claim 1, wherein a fused Hidden Markov Model (HMM) algorithm is used to obtain two or more temporal sequences at the same time, so as to enhance an interaction and characterization for dynamically representing a state at one moment for activity recognition, wherein if one HMM fails to obtain the accelerating data, another HMM is able to pick the accelerating data to ensure a stability of the pedometer.

5. The pedometer, as recited in claim 4, wherein the accelerometer is set at 25 Hz so that no more than 5 steps are counted within 25 of the consequent X values, and eight or more the consequent X values are collected for counting the one step motion.

6. The pedometer, as recited in claim 1, wherein when the pedometer is horizontally supported at the foot of the user, the accelerometer is initiated to automatically define the X axis, Y axis and Z axis with respect to a horizontal.

7. The pedometer, as recited in claim 1, wherein when the pedometer is inclindedly supported at the foot of the user, the accelerometer is initiated to automatically define the X axis, the Y axis and the Z axis with respect to the pedometer.

8. The pedometer, as recited in claim 1, further comprising a sensor which is configured to automatically activate the accelerometer and is selected from a group consisting of pressure sensor and motion sensor.

9. The pedometer, as recited in claim 8, wherein the sensor is a pressure sensor when the pedometer is embedded in a shoe worn on the foot of the user, such that when the user applies pressure, the pedometer is automatically activated to activate the accelerometer for data collection.

10. The pedometer, as recited in claim 8, wherein the sensor is a motion sensor such that when the user moves the foot thereof, the pedometer is automatically activated to activate the accelerometer for data collection.

* * * * *